United States Patent
Nielsen et al.

(10) Patent No.: US 7,067,252 B2
(45) Date of Patent: Jun. 27, 2006

(54) METHOD FOR GENOME MINING FOR SECRETED PROTEIN GENES

(75) Inventors: Preben Nielsen, Hørsholm (DK); Birthe Ravn Jørgensen, Søborg (DK)

(73) Assignee: Novozymes A/S, Bagsvaerd (DK)

( * ) Notice: Subject to any disclaimer, the term of this patent is extended or adjusted under 35 U.S.C. 154(b) by 339 days.

(21) Appl. No.: 09/882,144

(22) Filed: Jun. 15, 2001

(65) Prior Publication Data

US 2002/0106651 A1 Aug. 8, 2002

Related U.S. Application Data

(60) Provisional application No. 60/213,376, filed on Jun. 23, 2000.

(30) Foreign Application Priority Data

Jun. 21, 2000 (DK) ............................... 2000 00963

(51) Int. Cl.
*C12Q 1/70* (2006.01)
*C12Q 1/68* (2006.01)
*C12N 15/00* (2006.01)
*C12P 21/06* (2006.01)
*C07H 21/04* (2006.01)

(52) U.S. Cl. .................. 435/6; 435/4; 435/5; 435/69.1; 435/320.1; 435/DIG. 1; 435/DIG. 2; 435/DIG. 3; 536/23.1; 536/23.2

(58) Field of Classification Search .................. 435/6, 435/4, 5, 7.1, 69.1, 69.2, 471, 320.1, 256.1, 435/DIG. 1, DIG. 2, DIG. 3, DIG. 37; 536/23.1, 536/23.2

See application file for complete search history.

(56) References Cited

U.S. PATENT DOCUMENTS

| | | | | |
|---|---|---|---|---|
| 5,171,674 A | * | 12/1992 | Stevens et al. | ............. 435/69.1 |
| 5,506,126 A | | 4/1996 | Seed et al. | |
| 5,665,585 A | * | 9/1997 | Torkkeli et al. | ............. 435/203 |
| 6,165,718 A | * | 12/2000 | Borchert et al. | ............... 435/6 |

FOREIGN PATENT DOCUMENTS

WO    WO 89/08114    9/1989

OTHER PUBLICATIONS

Rehman et al (Molecular and Biochemical Parasitology, 97 (1998) 55-68).*
Lueking et al., Analytical Biochemistry 270, 103-111 (1999).

* cited by examiner

*Primary Examiner*—Padmashri Ponnaluri
(74) *Attorney, Agent, or Firm*—Jason Garbell

(57) ABSTRACT

The present invention relates to a method for screening for compounds secreted by an organism, comprising
(a) raising antibodies against secreted products of a donor organism,
(b) providing a gene library from the donor organism,
(c) cloning the gene library into a suitable host organism,
(d) expressing the cloned genes in the host organism, and
(e) detecting positive clones, which upon expression of the cloned genes secretes a compound, using the antibodies of (a) to identify such positive clones.
The invention also relates to compounds, nucleotide sequences and microorganisms identifiable by said method.

12 Claims, No Drawings

METHOD FOR GENOME MINING FOR SECRETED PROTEIN GENES

CROSS-REFERENCE TO RELATED APPLICATIONS

This application claims, under 35 U.S.C. 119, priority of Danish application no. PA 2000 00963, filed Jun. 21, 2000, and the benefit of U.S. application No. 60/213,376 filed Jun. 23, 2000, the contents of which are fully incorporated herein by reference.

FIELD OF THE INVENTION

The present invention relates to a method for mining genomes for genes encoding proteins and peptides, including enzymes, that are secreted from organisms, in particular microorganisms such as bacteria and fungi. The method uses immunoassay techniques to identify clones expressing genes encoding enzymes or other proteins or peptides that are secreted from an organism of interest.

BACKGROUND OF THE INVENTION

A typical bacterial genome is about 3–8 mB (mega base pairs) in size. For example, the Bacillus subtilis genome is known to have a size of 4.2 mB and to contain a total of 4100 protein coding genes. The function of 1200 gene products of Bacillus subtilis has been experimentally identified. The function of 42% of the genes could at the time the genome sequence was finished not be predicted by similarity to known genes encoding proteins with known function. These genes could be divided into three groups: 12% showed similarity to other genes with unknown function from other organisms, while 4% showed similarity to other genes with unknown function in *B. subtilis* only. The remaining 26% did not show homology to anything (F. Kunst et al. 1997. The complete genome sequence of the Gram-positive bacterium *Bacillus subtilis*. Nature 320:249–256).

Screening for enzymes, or other proteins or peptides, normally involves gene cloning in order to obtain a reasonable yield of a given enzyme encoding a desired product. Constructing a gene library, where the genome is cut into fragments, which are then ligated into a vector and transformed into a cloning host, does this. If the genome of *B. subtilis* is randomly cut into fragments with an average size of 4 kB (kilo base pairs), at least about 1000 clones must be screened in order to cover the entire genome once. In order to ensure that all open reading frames of the genome are represented in full length, a much higher number of clones must be screened in order to ensure that the entire genome is expressed. Usually the number of screened clones is on the order of magnitude of 5000–10,000 clones.

The genomes of *Aspergillus nidulans* and *Neurospora crassa* are known to have a size of 31.0 mB and 42.9 mB of DNA, respectively (Dunn-Colemann N. & Prade, R. 1998. Toward a global filamentous fungus genome sequencing effort. Nature Biotechnology, 16, 5; Radford and Parish, 1997. The genome and genes of *Neurospora crassa*. Fungal Genetics and Biology, 21, 258–266). The nuclear genome of *Saccharomyces cerevisiae* contains 13.0 mB, and about 6200 open reading frames have been predicted (Zagulski, M., Herbert C. J. & Rytka, J 1998. Sequencing and functional analysis of the yeast genome. Acta Biochimica Polonica, 45, 627–643).

A screening for enzymes in fungi can be based on an expression-cloning method, which combines the ability of *Saccharomyces cerevisiae* to express heterologous (fungal) genes with the utilization of enzyme assays. The fungus of interest is fermented under conditions that give high-level enzyme activity; mRNA is prepared from the resulting biomass and a cDNA library is constructed in *E. coli*. Plasmid DNA is isolated from subpools of this library and transformed into *S. cerevisiae*. Subsequently, the yeast transformants are screened for enzyme activity.

We assume that for a fungal genome about 5000 genes are expressed. For statistical reasons, and due to the manner in which cDNA is prepared, a high number of clones must be screened in order to ensure that all expressed enzymes are identified, i.e. on the order of magnitude of 50,000–100,000.

For a typical screen for any given enzyme or other gene product, a functional assay is applied: for example, proteases are screened in an assay specific for proteases, amylases are screened in an assay specific for amylases and so forth. The existing methods for traditional functional screening for extra-cellular enzymes are substantially limited to the applied screening assays. This means that screening of a genome provides a) only those enzymes for which a functional assay exists or can be designed, and b) only a single enzyme activity (or a very limited number of enzyme activities), i.e. the enzyme activity/activities that the assay is specific for or which can be derived from a single screening. Frequently, the same gene library is screened over and over again because it is desired to investigate several activities. This is ideally done in parallel, but as it is often not known at the outset which enzymes are of potential interest, gene libraries have to be newly constructed from the given wild type organism or the library has to be screened several times in the various functional assays. This method for screening for enzymes or other proteins has the disadvantage of being both time-consuming and expensive.

An estimate of the total number of extracellular enzymes in *B. subtilis* was made by 2D gel analysis of extracellular enzymes, and subsequent identification of spots by N-terminal sequencing. The number was predicted to be 150–180 extracellular enzymes (Hirose et al. 2000. Proteome analysis of *Bacillus subtilis* extracellular Proteins: a two dimensional protein electrophoretic study. Microbiology 146:65–75). This means that with a screening procedure designed to identify all secreted gene products, the number of hits would be about 200 clones from the total of 4100 open reading frames. In other words, if 10,000 clones are screened, 200–500 clones will carry a DNA fragment from the original genome expressing an extra-cellular protein or peptide. With a pre-screening for clones producing extra-cellular enzymes functional screening, should, in the ideal situation, be able to be performed on these less than 500 clones.

For fungi, the number of secreted gene products is assumed to be in the range of about 500–1000 for a given genome, so that only about 500–1000 clones from a total of approximately 25,000–40,000 screened clones are of real interest.

A tremendous savings in both time and money could be achieved by mining the gene libraries or cDNA libraries for clones expressing extracellular products. In a typical example of screening of a bacterial genome, the gene library could thus be initially screened in a secretion assay in which 5000–10,000 clones are screened and the approximately 200 clones are detected that encode secreted gene products. These 200 clones could then be screened using e.g. functional assays.

This means that compared to a theoretical screening procedure based only on functional assays in which a gene library might be screened in 200 different functional assays to detect all secreted gene products (e.g. 5000 clones× 200=1,000,000 screened clones), in the ideal case in which clones producing secreted products may be initially identified, the gene library is screened once for secreted products (e.g. 5000 clones) and the resulting approximately 200 secreted clones can subsequently be fingerprinted for biochemical activity in functional assays. Assuming again use of the same 200 functional assays, a total of only 200=200=40,000 clones would have to be investigated, in other words only 4% of the 1,000,000 clones that would have to be investigated using a functional assay alone.

Typically, a gene library might be screened using about 10 different functional assays. With 5000 clones this gives a total of 50,000 clones that must be screened. In the ideal case in which clones producing secreted gene products can be identified at the outset, the 5000 clones are screened once, after which all secreting clones are detected and analysed in the 10 functional assays, corresponding to a screening workload of 200 clones screened in 10 assays, i.e. only 2000 clones need to be screened in the functional assays, again a total of only 4% of the number of clones that must be screened using the functional assays alone.

For fungal cDNA libraries, the same statistical considerations apply.

In short, it would be a tremendous advantage to have a screening assay for secreted enzymes and other proteins from gene libraries wherein the relatively few clones producing secreted gene products could be identified at the outset, so that only these few clones have to be investigated in functional assays aimed at identifying proteins of interest. The present invention provides such an assay.

Prior art includes disclosures such as WO 89/08114 and Analytical Biochemistry, Vol. 270 (1) pp. 103–111 (1999), which relates to the use of specific monoclonal antibodies to identify compounds such as expression product, e.g. surface bound antigenic products. The prior art techniques do however not pertain to solving the problem of identifying unknown compounds for which no suitable antibody can be identified.

SUMMARY OF THE INVENTION

The present invention provides a novel screening method that makes it possible to screen the genome of a microorganism only once in order to identify all gene products secreted by the microorganism. Clones producing these secreted gene products may then easily and quickly be further screened for peptides or proteins having a desired function, e.g. enzymatic activity, and/or they may be subjected to nucleotide sequencing in order to identify genes encoding compounds of interest.

In a first aspect, the invention relates to a method for screening for compounds secreted by an organism, comprising (a) Raising antibodies against secreted products of a donor organism,
(b) providing a gene library from the donor organism,
(c) cloning the gene library into a suitable host organism,
(d) expressing the cloned genes in the host organism, and
(e) detecting positive clones, expressing a cloned gene encoding a secreted compound, using the antibodies of (a) to identify such positive clones.

The invention also in a second aspect relates to a novel compound obtained or obtainable by the method of the invention.

In a third aspect the invention relates to a method for screening for a nucleotide sequence encoding a compound secreted by an organism comprising steps (a) to (e) of the first aspect and the additional step of subjecting at least one positive clone to nucleotide sequencing to identify at least one nucleotide sequence encoding a secreted compound.

In a fourth aspect the invention relates to a nucleotide sequence obtained or obtainable by the method of the third aspect.

In a fifth aspect the invention relates to a method for screening microorganisms for strains that secrete a compound comprising step (a) of the first aspect and the additional step of subjecting the microorganism to an immunoassay using the antibodies from step (a) of the first aspect to identify microorganisms that secrete said compound.

In a sixth aspect the invention relates to a microorganism obtained or obtainable by the method of any of the fifth aspect.

DETAILED DESCRIPTION OF THE INVENTION

In the context of the present specification and claims, the term "secreted compound" refers to any compound that is secreted by a microorganism of interest. The compound may be associated with the membrane of the microorganism, but in particular a preferred secreted compound is a compound, which is secreted/transported by the microorganism beyond the cellular boundaries into the extracellular medium surrounding the cell entity. Secreted compounds include in particular, but are not limited to, proteins and peptides.

One object, which is solved by the present invention, is to find a method for identifying secreted compounds for which no functional assay exist and/or no antibody is known. Another object, which is solved by the present invention, is to find a method in which several, i.e. more than one, secreted component from a donor could be identified simultaneously, thus speeding up screening methods. A third object, which is solved by the present invention, is to find a method suitable for screening only secreted compounds.

As indicated above, secreted compounds such as enzymes are of particular interest. The enzymes screened for in accordance with the invention may belong to known classes of enzymes, or they may be of unknown enzyme classes, e.g. enzymes having a desired functional activity but not necessarily belonging to a known enzyme class. As used herein, the term "enzyme class" (E.C.) refers to the internationally recognized enzyme classification system, Recommendations (1992) of the Nomenclature Committee of the International Union of Biochemistry and Molecular Biology, Academic Press, Inc., 1992.

The types of enzymes which may appropriately be identified include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)], while preferred transferases are transferases in any of the following sub-classes:
a) Transferases transferring one-carbon groups (EC 2.1);
b) Transferases transferring aldehyde or ketone residues (EC 2.2); acyltransferases (EC 2.3);
c) Glycosyltransferases (EC 2.4);
d) Transferases transferring alkyl or aryl groups, other than methyl groups (EC 2.5); and
e) Transferases transferring nitrogeneous groups (EC 2.6).

A most preferred type of transferase in the context of the invention is a transglutaminase (protein-glutamine γ-glutamyltransferase; EC 2.3.2.13).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases. Other preferred hydrolases are xyloglucanase, arabinase, rhamnogalactoronase, pectinases, ligninases (for example polyphenol hydrolase).

In the present context, the term "carbohydrase" is used to denote not only enzymes capable of breaking down carbohydrate chains (e.g. starches) of especially five-and six-membered ring structures (i.e. glycosidases, EC 3.2), but also enzymes capable of isomerizing carbohydrates, e.g. six-membered ring structures is such as D-glucose to five-membered ring structures such as D-fructose.

Carbohydrases of relevance include the following (EC numbers in parentheses): α-amylases (3.2.1.1), β-amylases (3.2.1.2), glucan 1,4-α-glucosidases (3.2.1.3), cellulases (3.2.1.4), endo-1,3(4)-β-glucanases (3.2.1.6), endo-1,4-β-xylanases (3.2.1.8), dextranases (3.2.1.11), chitinases (3.2.1.14), polygalacturonases (3.2.1.15), lysozymes (3.2.1.17), β-glucosidases (3.2.1.21), α-galactosidases (3.2.1.22), β-galactosidases (3.2.1.23), mannanase (3.2.1.25), amylo-1,6-glucosidases (3.2.1.33), xylan 1,4-β-xylosidases (3.2.1.37), glucan endo-1,3-β-D-glucosidases (3.2.1.39), α-dextrin endo-1,6-α-glucosidases (3.2.1.41), sucrose α-glucosidases (3.2.1.48), glucan endo-1,3-α-glucosidases (3.2.1.59), glucan 1,4-β-glucosidases (3.2.1.74), glucan endo-1,6-β-glucosidases (3.2.1.75), endo-1,4-β-mannanase, (3.2.1.78), arabinan endo-1,5-α-L-arabinosidases (3.2.1.99), endo-1,6-β-mannanase (3.2.1.101), lactases (3.2.1.108), chitosanases (3.2.1.132) and xylose isomerases (5.3.1.5).

However enzymes nor yet classified is particularly relevant for the present invention.

Examples of other proteins and peptides that may be screened for in accordance with the invention are: receptor binding peptides such as hormones or peptide antibiotics.

The term "organism" and refers to any organism that is capable of producing and secreting compounds of interest, including micro-organisms. In the perspective of screening for compounds, which may be produced in industrial scale volumes, preferred donor organisms are prokaryotic cells such as bacteria and/or eukaryotic fungal cells. However other organisms such as cell cultures of human or other mammal or other animal or plant cells ay be used. Of particular interest in the context of the present invention are methods for screening donor micro-organisms for secreted compounds of interest. Once identified, the gene encoding a secreted compound of interest can of course be transferred to any suitable host strain (typically a bacteria or fungus) for e.g. production of said compound.

The term "donor organism" refers to any of the organisms as defined above when used in the screening method of the invention to generate a gene library.

The term "host organism" refers to any of the organisms into which a gene library of a donor strain can be displayed.

The term "gene library" includes both libraries of genomic nucleotide sequences, libraries of cDNA sequences and all other types of libraries of nucleotide sequences derived from a donor organism, e.g. a genomic DNA library obtained from a donor strain in accordance with the screening method of the invention. Preferably a gene library contains the entire genomic DNA or the entire cDNA from a donor organism.

The term "primary antibodies" refers to antibodies raised against a compound or a mixture of compounds secreted by the donor strain. The primary antibodies are preferably polyclonal and recognises the compound or compounds secreted by the donor organism. In a preferred embodiment the primary antibodies are raised against compounds present in the supernatant of a donor organism culture liquid and/or a broth from the fermentation of a donor organism. In the present screening method such primary antibodies will be capable recognising all compounds in the culture supernatant, i.e. secreted extracellular compounds. In another preferred embodiment the primary antibody or mixture of antibodies is raised against secreted extracellular compounds as well surface bound compounds. In the present screening method such antibody mixture will be capable recognising secreted compounds including secreted extracellular compounds and surface bound compounds being exposed to the extracellular medium. The primary antibodies may be labelled primary antibodies enabling detection of presence of a compound from the donor organism directly, or the primary antibodies may be recognized by secondary antibodies. In a preferred embodiment the primary antibodies are a mixture of antibodies prepared by immunization of an animal with the culture supernatant of a donor organism or a culture supernatant including surface bound compounds of the donor organism and isolating the mixture of antibodies formed in the animal against secreted compounds of the culture supernatant.

The term "secondary antibodies" refers to labelled antibodies specifically recognizing the primary antibodies and enables detection of a bound primary antibody.

The terms "labelled primary antibodies" and "labelled antibodies" refer to antibodies labelled with a marker in order to detect their presence in a sample. This could be either by emission of radiation, by an enzyme reaction or by fluorescence.

The terms "heterologous expressed compound" and "heterologous expressed DNA" refer to a protein or other compound, respectively to genes of the donor organism expressed in a heterologous host organism that could be but are nor restricted to B. subtilis, E. coli, S. cerevisia or A oryza The term "positive clone" refers to any host organism which (1) comprises a nucleotide sequence from a gene library derived from a donor organism under investigation, (2) upon cultivation produces and/or secretes a compound which gives an immuno-reaction with primary antibodies, thereby enabling discrimination of said positive clone from other clones that also comprises a nucleotide sequence from a gene library derived from the donor organism, but do not produce and/or secretes a compound recognizable by primary antibodies.

The term "additional screening step" refers to any screening step performed in addition to the immunoassay screening of the invention. The additional screening step may in particular be a functional assay, for example an enzyme assay, in which the function of said cloned gene is identified, or a receptor assay in which a secreted peptide binds to a receptor, or an antimicrobial assay in which an antimicrobial peptide interacts with a microorganism (bacterium or fungus).

According to the method of the invention, immunoassay techniques are used to identify clones that produce a secreted gene product. A major advantage of this method is that even unknown gene products— for example an enzyme with no known biological function— can be detected. For such an enzyme, no functional screening assay will be available, but such enzymes will be detected in a screening directed to secreted gene products.

The invention is a method for mining genomes of genes encoding all compounds secreted by a selected donor organism.

A culture supernatant is produced by cultivation of a donor organism. Cells are separated from the supernatant. The supernatant, optionally including compounds bound or associated to the cell membrane, is used for immunization, so antibodies are raised against secreted compounds produced by the donor organism. The supernatant may be used directly for this immunisation process or it may be refined prior to the immunisation process, e.g. by removing undesired compounds or adding desired compounds. However, as it is evident from objects of the present invention, that it is to be understood that refinement of the supernatant do not include separating the secreted compounds into single discrete secreted compounds, and using these discrete secreted compounds to raise discrete antibodies, because such procedure would not provide the advantages of the present invention. Hence, it is essential to the invention, that the supernatant or mixture of secreted compounds used to raise antibodies comprise at least 2 secreted compounds of the donor organism, preferably more than 3, more preferably more than 5, more preferably more than 7, most preferably more than 10 secreted compounds of the donor organism to be of use in the present invention.

In another embodiment the mixture of antibodies may also be refined after recovering the mixture of antibodies from the immunisation process, of course with the above mentioned proviso that the refinement do not include separating the antibodies into single discrete antibodies. As an example of refinement of antibodies, the antibodies may be treated to remove or reduce antibodies which exhibits cross reaction with secreted compounds of a host organism, which in the present invention hosts the gene library of the donor organism, so as to reduce the background emanating from the host itself.

In the immunisation process antibodies are raised against all compounds in the refines or unrefined supernatant, optionally including compounds bound or associated to the cell membrane. Methods of raising of antibodies, e.g. polyklonal antibodies are known to the art such as from: N. M. G. Harboe & A. Ingild:

Immunization, Isolation of Immunoglobulins and Antibody Titre Determination, Scand. J. Immunol., Vol. 17, Suppl. 10, pp 345–351, 1983.

A gene library comprising genomic DNA, preferably the entire genome of a donor organism or cDNA or mRNA, preferably the total mRNA of a donor organism may be constructed and inserted or cloned into a suitable host organism. The recovery of nucleotide material, insertion or cloning of the gene library into the host organism may be achieved by any suitable conventional method, such as transformation or transfection of the host organism with the library. Non-limiting examples of conventional methods for recovering nucleotide materials from a donor organism include the methods described in Pitcher et al., "Rapid extraction of bacterial genomic DNA with guanidium thiocyanate", Lett. Appl. Microbiol., 8, pp 151–156, 1989; Diderichsen et al., "Cloning of aldB, which encodes alpha-acetolactate decarboxylase, an exoenzyme from *Bacillus brevis*", J. Bacteriol., 172, pp 4315–4321, 1990; Dretzen et al., "A reliable method for the recovery of DNA fragments from agarose and acryla-mide gels", Anal. Biochem., 112, pp 295–298, 1981 or WO 94/19454. Non-limiting examples of conventional methods for cloning nucleotide sequences into a suitable host organism includes the methods described in Ausubel, et al. (eds.) Current protocols in Molecular Biology, John Wiley and Sons, 1995, Harwood, C. R., and Cutting, S. M. (eds.), "Molecular Biological Methods for *Bacillus*", John Wiley and Sons, 1990 or Sambrook et al., "Molecular cloning: A laboratory manual", Cold Spring Harbor lab., Cold Spring Harbor, N.Y. (1989).

Although the primary objective of the invention is to screen a host organism comprising a gene library from a donor organism for clones producing a compound which is identical to a compound produced by the donor organism itself, the screening method of the invention may also be used to screen for clones producing a compound which is not completely identical to a compound produced by the donor organism itself, but which exhibits cross reactivity with primary antibodies. Cross reactivity between an antibody raised against compound produced by the donor organism and a non identical compound of a host organism requires a certain degree of similarity, but some differences in form of mutations and/or substitutions could be allowed, while preserving the feasibility of the present invention. Accordingly the gene library from the donor organism may be subjected to manipulation before cloning it into a suitable host cell e.g. by gene shuffling, such as described by Stemmer, Proc. Natl. Acad. Sci. USA, 91, pp. 10747–10751, 1994 and Stemmer, Nature, 370, pp. 389–391, 1994; and/or by random mutagenisis as described by Eisenstadt et al., "Gene mutation", Methods for general and molecular bacteriology, pp. 297–316, Eds: Gerhardt P., Murray R. G. E., Wood W. A. and Krieg N. R., ASM, 1994.

Accordingly the invention encompasses screening methods wherein nucleotide sequences in the gene library of the donor organism have been mutated. In this context it is also possible by using the method of the invention to prepare gene libraries from other organisms than the donor organism, so as to identify secreted compounds from one or more other organisms which is sufficiently similar to secreted compounds for the donor organism to provide for cross reactivity with primary antibodies.

The clones of the host organism comprising the library are screened using the antibodies raised against the culture supernatant of the donor organism, optionally including compounds bound or associated to the cell membrane. Screening with antibodies can be performed in multiple ways, wherein, however, the basic principle is the same: 1) the antibody binds to the antigen. (2) Binding of antibodies is detected. Some ways of doing this includes:

Colony Hybridization:
1) clones comprising the gene library is spread on agar plates
2) clones are cultivated
3) protein or other secreted compounds are immobilised on membrane or filter
4) primary antibodies are hybridized to the filter
5) detection of bound antibodies either with labelled secondary antibodies or directly with labelled primary antibodies.

Methods for colony hybridisation are known e.g. from Kragelund et al.; "Outer membrane protein heterogeneity within *Pseudomonas fluorescens* and *P. putida* and use of an OprF antibody as a probe for rRNA homology group I pseudomonads"; Applied and Environmental Microbiology, Vol. 62 (2) pp. 480–485 (1996).

Dot Blot Hybridization:
1) clones comprising the gene library are cultivated e.g. in micro plates.
2) supernatant or culture fluid is transferred to a hybridization membrane.
3) protein or other secreted compounds are immobilised on membrane or filter
4) primary antibodies are hybridized to the filter
5) detection of bound antibodies either with lablled secondary antibodies or directly with labelled primary antibodies.

Methods for dot blot hybridisation are known e.g. from Hawkes et al.; "A Dot Immuno Binding Assay for Mono Clonal and other Antibodies"; J. Analytical Biochemistry, Vol. 119 (1) pp. 142–147 (1982)

ELISA Method a
1) clones comprising the gene library are cultivated e.g. in micro plates.
2) protein or other secreted compounds are immobilised on the micro plate
3) primary antibodies are hybridized to the filter
4) detection of bound antibodies either with labelled secondary antibodies or directly with labelled primary antibodies.

ELISA Method b
1) clones comprising the gene library are cultivated e.g. in microplates.
2) primary antibodies are bound to another micro plate
3) supernatant or culture fluid with protein or other secreted compounds added to the plate coated with antibodies
4) detection of bound protein or alternative compound with labelled primary antibodies.

Methods for ELISA are known e.g. from Kirkegaard & Perry Laboratories. 1999 Product catalog. p. 66

Protein Micro Array:
1) clones comprising the gene library are cultivated e.g. in micro plates.
2) protein or other secreted compounds in the supernatant are immobilised on a microscope slide coated with Nylon or nitrocellulose
3) primary antibodies are hybridized to the filter
4) detection of bound antibodies either with labelled secondary antibodies or directly with labelled primary antibodies.

Methods for Protein micro array are known e.g. from Lueking et al.; "Protein microarrays for gene expression and antibody screening"; Analytical Biochemistry, Vol. 270 (1) pp. 103–111 (1999)

After screening the clones comprising the gene library, positive clones may be subjected to nucleotide sequencing using methods known per se in the art. The open reading frames of the corresponding inserts are determined and the corresponding gene identified. The gene may then be identified as falling into a known class of genes for which the functionality of the gene products are known, or it may encode an unknown secreted product. Compared to the currently applied approach of whole genome sequencing, the method of the invention provides significant advantages in terms of speed and economy. Methods for nucleotide sequencing are known in the art e.g. from Lee et al.; "New energy transfer dyes for DNA sequencing"; Nucleic Acids Research, 1997, vol. 25, No. 14.

Further after the screening, the identified positive clones may be subjected to additional screening steps e.g. to verify to the screening results and/or to achieve more specific differentiation between the positive clones. For verification the positive clones may be subjected to at least one additional screening comprising cultivating said positive clones and assaying them in a second immunoassay using the same antibodies as used in the first immunoassay to eliminate possible false positives.

Additional screening steps to achieve differentiation between the positive clones include subjecting the clones to functional assays, wherein functional properties of produced compounds are investigated. For enzyme compounds preferred functional properties includes but is not limited to wash performance, thermal stability, substrate specificity, catalytic turnover, oxidation stability, sensitivity to inhibitors, pH optimum, detergent stability, stability against microbial inactivation etc. For receptor binding peptides or peptide antibiotics preferred functional properties includes but is not limited to toxicology, distribution profile in the human or animal body, metabolisation products, side effects, rate of metabolisation or secretion, receptor binding capacity, antimicrobial capacity etc. Preferably additional screening steps are performed using as a starting material to be tested a supernatant obtained from cultivating positives clones or a refined and/or purified product thereof.

Enzymes and other proteins with unknown functions can prove to be of significant value in order to solve important needs. For example, in relation to enzymes used in laundry detergents, certain stains are known to be removable with known enzymes. However, it is desirable to be able to identify new enzymes or proteins that could be useful for removing such stains or other stains, although for this purpose the chemical nature of the stain is not necessarily known and the biochemical nature of the enzyme does not need to be known. By using a random approach based on identifying secreted enzymes or proteins in accordance with the invention, all secreted enzymes and other proteins of a given genome can be tested directly in a stain removal assay. This assay may for practical reasons not be applicable as a direct screening assay. Since the number of enzymes to be tested in this manner is very limited compared to the total number of gene products in the genome as a whole, the functional assay used to identify enzymes with a desired activity can be performed quickly and easily.

In relation to baking or other complex food processes enzymes may on the one hand catalyze reactions leading to useful products either in terms of taste, smell or texture. On the other hand enzymes may as well remove substrates that gives unwanted properties such as bad smell or odour or structure. These reactions are not always obvious, and substrates and products are not necessarily known or may even be impossible to characterize. High throughput assays are not possible to do for such reactions. For this reason a pre-selection as disclosed herein is necessary.

In relation to animal feed enzymes may facilitate digestion and make feed better accessible or may even release useful compounds for the animal. Such assays may demand testing on animals. Also here a pre-selection is necessary in order to reduce the number of tested animals.

In relation to textile, it is well known that various hydrolytic enzymes are useful in the processing of especially cotton fabrics and yarn. The structure and the components of cotton are not fully known or understood, and for this reason enzymes of unknown function are useful. However, throughput in such tests is limited and again pre-selection is demanded.

A screening approach that detects secreted gene products in an initial step has a strong impact on the speed of the screening, the throughput needed, and the machinery and resources needed. Furthermore, this screening approach can also have a substantial impact on the nature of the encoded gene products to be identified. For example, a beneficial effect may be obtained where gene libraries from more that one genome are constructed and screened collectively, e.g. in environmental samples. It has been shown that a small sample of soil (e.g. 1 g) typically contains a variety of different microorganisms, containing both cultivable and so-called non-cultivable organisms (where the term "non-cultivable" refers to organisms that cannot be cultivated in any known medium) corresponding to 4000 different genomes (Torsvik et al. 1990. Comparison of phenotypic diversity and DNA heterogeneity in a population of soil bacteria, Appl. Environ. Microbiol., 56: pp 776–781). Typically, several hundred thousand clones are screened in a given functional assay to detect clones carrying a desired activity. Again, by using a secretion assay according to the invention, organisms, which is different from a donor organism from which secreted compounds antibodies are raised, which secretes similar compounds can be identified and in case of screening of gene libraries from such organisms a significantly lower number of clones need to be screened, which can have a drastic effect on the throughput and workload.

The above-described system could also be applied to a consortium of organisms subjected to a multi-resistant pathogenic bacterium. Under such conditions, antimicrobial agents would be induced. Subsequently, the method could selectively mine the library of the entire consortium for clones expressing antimicrobial agents.

The above-mentioned system could be applied for a consortium of organisms subjected to a bacterium that might be multi resistant to known antibiotic and might be pathogenic to humans animals or plants. Under such conditions antimicrobial agents would be induced. Subsequently the method could selectively mine the library of the entire consortium for clones expressing antimicrobial agents. It is impossible to perform such tests with the extremely high throughput of a normal procedure. However, it will be possible by using the antibody mining disclosed here.

With cell cultures the method can be applied for mining for otential receptor binding compounds.

Summarizing, the present invention provides a new approach in which e.g. a bacterial or fungal genome is screened only once in order to detect all secreted gene products. These secreted gene products can then be subjected to additional assays, such as specific functional screening assays, to identify clones of interest and for e.g. identifying novel compounds with a desired activity.

The invention will be further illustrated in the following non-limiting examples.

EXAMPLES

Example 1

Screening for Multiple Proteins by Colony Hybridisation

Production of Antibodies

Polyclonal antibodies against extra-cellular enzymes from a bacterium, Bacillus agaradhaerens strain AC13, was made by cultivation of the strain in BPX medium supplemented with 100 mM NaHCO$_3$ at 30° C. for 5 days with agitation at 250 RPM (BPX medium is: potato flour 100 g/l, barley flour 50 g/l, sodium caseinate 10 g/l, soy-bean cake 20 g/l, Na$_2$HPO$_4$, 12H$_2$O, 9 g/l and Pluronic 0.1 ml/l autoclaved in 100 ml aliquots for 40 min at 120° C.). The supernatant of 50 ml of the culture was recovered by centrifugation at 3000 RPM, and concentrated by freeze drying. Subsequently, the freeze dried protein was re-suspended in 10 ml of water, sterile filtered and used for raising antibodies in rabbit (The immunisation, and recovery of antibodies provided by DAKO, Copenhagen, Denmark). These antibodies was referred to as "primary antibodies".

Genomic DNA Preparation

*Bacillus agaradhaerens* strain AC13 was propagated in LB medium to which 100 mM NaHCO$_3$ had been added. After 16 hours of incubation at 30° C. and 300 RPM, the cells were harvested, and genomic DNA was isolated by the method described by Pitcher et al. (Pitcher, D. G., Saunders, N. A., Owen, R. J . 1989. Rapid extraction of bacterial genomic DNA with guanidium thiocyanate; Lett. Appl. Microbiol. 8:151–156). (LB was: 25 g/l of LB bouillon Merck Art. 0285; for agar 15 g/l of Bacto-agar Difco Art. 0140 was added prior to autoclaving).

Genomic Library Construction

Genomic DNA was partially digested with restriction enzyme Sau3A and size-fractionated by electrophoresis on a 0.7% agarose gel. Fragments of between 2 and 7 kB in size were isolated by electrophoresis onto DEAE-cellulose (Dretzen G, Bellard M, Sassone-Corsi P7 Chambon P. 1981. A reliable method for the recovery of DNA fragments from agarose and acrylamide gels; Anal. Biochem. 112 295–298). Isolated DNA fragments were ligated to BamHI digested pSJ1678 plasmid DNA.

Ligated DNA was used in electroporation of *E. coli* SJ2, or *B. subtilis* PL 3350. The transformed cells were plated onto LB-agar plates containing 10 ppm (for *E. coli*) or 6 ppm (for *B. subtilis*) chloramphenicol, and the agar plates were incubated for 18 hours at 37° C.

Colony Hybridisation

The resulting colonies were blotted to a nitrocellulose filter (Schleicher & Schuell Art. 10401116) by incubating the agar plate with the filter on top for 2 h at room temperature. The filter was incubated for 10 min in a blocking solution, incubated in washing buffer pH 10 to which 1000× diluted primary antibodies was added, washed three times in washing buffer, incubated in washing buffer to which 1000× diluted anti-rabbit antibody (secondary antibody, Art. No. P0217, DAKO, Copenhagen) conjugated with horse radish peroxidase (HRP) had been added, washed three times in washing buffer, washed once in acetate buffer pH 5.5, and incubated in staining solution to develop color. All these steps were carried out at room temperature and with agitation, 50 RPM. Positive clones were detected by the formation of red spots on the filter.

Solutions for Colony Hybridization

Washing buffer: TRIS Merck Art. 108382, 6 g/l; Sodium chloride Merck Art. 106404, 8.75 g/l and Tween 20 Merck Art. 822184, 0.5 g/l in deionised water, pH 10

Blocking solution: Tween 20 Merck Art. 822184, 20 g/l in washing buffer

Acetate buffer pH 5.5: Sodium acetate Merck Art. 106267, 6.8 g/l, and acetic acid Merck art. 100063, 1.8 ml/l in deionised water.

Staining solution: 3-amino-9-ethylcarbazole stock 40 ml/l, Hydrogen peroxide Merck Art. 7209, 0.5 ml/l.

3-amino-9-ethylcarbazole stock: 5 g/l of 3-amino-9-ethylcarbazole Sigma Art. A-5754 in absolute ethanol.

Positive clones were recovered from the agar plate and fermented in LB broth containing 6 ppm chloramphenicol for 2 days at 37° C. with agitation at 250 RPM. Cells were removed by centrifugation, 5 ml supernatant was loaded onto a 10% Bis-Tris gel (Novex Art. P0217). The gel was run as recommended by the manufacturer. The gel was then blotted to a nitrocellulose filter (BA85 Protran, Schleicher & Schuell) using a semi-dry blotter (Semi dry blotter II, Kem-En-Tec, Denmark). The filter was hybridised and stained as described above. A positive hit was seen as a discrete band on the filter.

Example 2

Screening for Multiple Proteins with Dot Blot Hybridisation of Supernatants in Micro-Plates The DNA library of Example 1 was plated out and cultivated as described above. Colonies were picked from plates and transferred to micro-plates using an automated colony picker (Flexys colony picking station, Genomic Solutions Inc., Ann Arbor). The DNA library was grown in micro-plates as described for liquid fermentation above.

The plates were centrifuged and supernatants were transferred to a nitrocellulose filter. The filter was hybridised and stained as described above. Samples of 1 µl of culture supernatants from cultures grown in TY broth for 1 to 3 days were loaded to the filter. Red spots on the filter indicated a reaction with the antibodies.

Example 3

Screening for Multiple Proteins with Protein Arrays

The DNA library of Example 1 was plated out and cultivated as described above. Colonies were picked from the plates and transferred to micro-plates using an automated colony picker (Flexys colony picking station, Genomic Solutions Inc, Ann Arbor). The DNA library was grown in micro-plates as described for liquid fermentation above. These plates were then centrifuged at 3000 RPM and supernatants were transferred to new micro-plates. The micro-plate supernatants were spotted onto a nitrocellulose-coated microscope slide (Oncyte Art. No. 70332, Electron Microscopy Sciences, Fort Washington, Pa.) using an arrayer (GMS417, Affymetrics, Santa Clara, Calif.). The array was hybridised as described above, except that the secondary antibody was anti-rabbit antibody labelled with Alexafluor-546 (Art. No. A-11035, Molecular Probes) The array was read using an array scanner (GMS418, Affymetrics, Santa Clara, Calif.). The sensitivity of this method was improved by making a normalisation to the total amount of protein loaded at the array using Sypro orange (Molecular Probes Art. S-6650) staining. The array was incubated for 5 minutes in Sypro orange diluted 5000× in washing buffer (see above) followed by a brief wash in washing buffer. Protein was measured as red fluorescence with the array scanner. Normalisation and identification of positive hits were made with the computer programs Genesight, Imagene, and Clonetracker (Affymetrics, Santa Clara, Calif.).

Example 4

Screening for Multiple Fungal Proteins with Protein Arrays

Production of Antibodies

Polyclonal antibodies against extra-cellular compounds from a fermented fungus, Humicola insolens, was made by (1) recovery of a Humicola insolens fermentation broth and raising antibodies in rabbit against the supernatant of this fermentation broth. The procedure was as described in example 1.

The antibody mixture raised against the extra-cellular compounds secreted from the Humicola insolens fermentation broth was evaluated by Western Blot analysis of relevant fermentation samples. This analysis revealed around 20 bands in the western blot demonstrating a broad spectrum of antibodies.

Pre-Treatment of Antibodies

The prepared antibody mixture was subjected to pre-treatment with the supernatant of an *A. oryzae* transformation host fermentation to reduce or eliminate background from transformation host. This background was probably caused by unspecific antibody response from glycosylated host proteins. The pre-treatment was carried out by mixing 100 µl antibody mixture with 400 µl *A. oryzae* supernatant and 5 ml tris malein buffer pH 7.0. This mixed solution was shaken for 2 hours at room temperature. After centrifugation at 4000 rpm the supernatant was mixed ad 100 ml with washing buffer pH 10, described in example 1.

The Tris/malein buffer, pH 7.0, was prepared by dissolving 1.2 g/l Malein acid and 2.6 g/l Tris 7–9 in water.

cDNA Library Construction

A EcoRI/NotI directional *Humicola insolens* cDNA library was constructed in a AMA1-containing *Aspergillus* expression vector based on the autonomously replicating element AMA as described in WO 00/24883 A1 (see page 2, line 17–26 and the examples on page 36, line 7 to page 40, line 3, incorporated herein by reference). The *H. insolens* poly(A)+RNA was isolated from a *H. insolens* production fermentation, 33 hours after fermentation start.

Double-stranded cDNA was synthesized from 5 µg of *Humicola insolens* poly(A)$^+$ RNA by the RNase H method (Gubler and Hoffman 1983, supra; Sambrook et al., 1989) using a hair-pin modification. The poly(A)$^+$RNA (5 µg in 5 µl of DEPC-treated water) was heated at 70° C. for 8 minutes in a pre-siliconized, RNase-free Eppendorf tube, quenched on ice, and combined in a final volume of 50 µl with reverse transcriptase buffer (50 mM Tris-Cl pH 8.3, 75 mM KCl, 3 mM MgCl$_2$, 10 MM DTT) containing 1 mM of dATP, dGTP and dTTP, and 0.5 mM of 5-methyl-dCTP, 40 units of human placental ribonuclease inhibitor, 4.81 µg of oligo(dT)$_{18}$-NotI primer (Amersham-Pharmacia Biotech, Uppsala, Sweden) and 1000 units of SuperScript II reverse transcriptase (Gibco-BRL, is USA).

First-strand cDNA was synthesized by incubating the reaction mixture at 45° C. for 1 hour. After synthesis, the mRNA:cDNA hybrid mixture was gel filtrated through a Pharmacia MicroSpin S-400 HR spin column according to the manufacturer's instructions.

After the gel filtration, the hybrids were diluted in 250 µl of second strand buffer (20 mM Tris-Cl pH 7.4, 90 mM KCl, 4.6 mM MgCl$_2$, 10 mM (NH$_4$)$_2$SO$_4$, 0.16 mM βNAD$^+$) containing 200 µM of each dNTP, 60 units of *E. coli* DNA polymerase I (Pharmacia, Uppsala, Sweden), 5.25 units of RNase H, and 15 units of *E. coli* DNA ligase. Second strand cDNA synthesis was performed by incubating the reaction tube at 16° C. for 2 hours, and an additional 15 minutes at 25° C. The reaction was stopped by addition of EDTA to 20 mM final concentration followed by phenol and chloroform extractions.

The double-stranded cDNA was ethanol precipitated at −20° C. for 12 hours by addition of 2 volumes of 96% ethanol and 0.2 volume of 10 M ammonium acetate, recovered by centrifugation, washed in 70% ethanol, dried (SpeedVac), and resuspended in 30 µl of Mung bean nuclease buffer (30 mM sodium acetate pH 4.6, 300 mM NaCl, 1 mM $ZnSO_4$, 0.35 mM dithithreitol, 2% glycerol) containing 25 units of Mung bean nuclease. The single-stranded hair-pin DNA was clipped by incubating the reaction at 30° C. for 30 minutes, followed by addition of 70 µl of 10 mM Tris-Cl, pH 7.5, 1 mM EDTA, phenol extraction, and ethanol precipitation with 2 volumes of 96% ethanol and 0.1 volume 3 M sodium acetate pH 5.2 on ice for 30 minutes.

The double-stranded cDNAs were recovered by centrifugation (20,000 rpm, 30 minutes), and blunt-ended with T4 DNA polymerase in 30 µl of T4 DNA polymerase buffer (20 mM Tris-acetate, pH 7.9, 10 mM magnesium acetate, 50 mM potassium acetate, 1 mM dithiothreitol) containing 0.5 mM of each dNTP, and 5 units of T4 DNA polymerase by incubating the reaction mixture at +16° C. for 1 hour. The reaction was stopped by addition of EDTA to 20 mM final concentration, followed by phenol and chloroform extractions and ethanol precipitation for 12 h at −20° C. by adding 2 volumes of 96% ethanol and 0.1 volume of 3M sodium acetate pH 5.2.

After the fill-in reaction the cDNAs were recovered by centrifugation as above, washed in 70% ethanol, and the DNA pellet was dried in a SpeedVac. The cDNA pellet was resuspended in 25 µl of ligation buffer (30 mM Tris-Cl, pH 7.8, 10 mM $MgCl_2$, 10 mM dithiothreitol, 0.5 mM ATP) containing 2 µg EcoRI adaptors (0.2 µg/µl, Pharmacia, Uppsala, Sweden) and 20 units of T4 ligase by incubating the reaction mix at 16° C. for 12 hours. The reaction was stopped by heating at 65° C. for 20 minutes, and then placed on ice for 5 minutes. The adapted cDNA was digested with NotI by addition of 20 µl autoclaved water, 5 µl of 10× NotI restriction enzyme buffer and 50 units of NotI, followed by incubation for 3 hours at 37° C. Heating the sample at 65° C. for 15 minutes stopped the reaction. The cDNAs were size-fractionated by agarose gel electrophoresis on a 0.8% SeaPlaque GTG low melting temperature agarose gel (FMC, Rockland, Me.) in 1×TBE (in autoclaved water) to separate unligated adaptors and small cDNAs. The gel was run for 12 hours at 15 V, and the cDNA was size-selected with a cut-off at 0.7 kb by cutting out the lower part of the agarose gel. Then a 1.5% agarose gel was poured in front of the cDNA-containing gel, and the double-stranded cDNAs were concentrated by running the gel backwards until it appeared as a compressed band on the gel. The cDNA-containing gel piece was cut out from the gel and the cDNA was extracted from the gel using the GFX gel band purification kit (Amersham, Arlington Heights, Ill.) as follows. The trimmed gel slice was weighed in a 2 ml Biopure Eppendorf tube, then 10 ml of Capture Buffer was added for each 10 mg of gel slice, the gel slice was dissolved by incubation at 60° C. for 10 minutes, until the agarose was completely solubilized, the sample at the bottom of the tube by brief centrifugation. The melted sample was transferred to the GFX spin column placed in a collection tube, incubated at 25° C. for 1 minite, and then spun at full speed in a microcentrifuge for 30 seconds. The flow-through was discarded, and the column was washed with 500 µl of wash buffer, followed by centrifugation at full speed for 30 seconds. The collection tube was discarded, and the column was placed in a 1.5 ml Eppendorf tube, followed by elution of the cDNA by addition of 50 µl of TE pH 7.5 to the center of the column, incubation at 25° C. for 1 minute, and finally by centrifugation for 1 minute at maximum speed. The eluted cDNA was stored at −20° C. until library construction.

Ligated cDNA was used in electroporation of *E. coli* Electromax DH10B, and DNA amplification carried out. Library pools of approx. 20000 cfu were plated out, and Qiagen-purified pool DNA thereof was used for transformation in the *A. oryzae* host. Spore pools were harvested from Cove agar plates, and 29 pools was prepared, each pool representing 3 agar plates containing approx. 300 colonies.

Screening of cDNA Library by Using Protein Arrays

The cDNA library was inoculated and grown in 96 well low-protein-binding filtration plates (Millipore, MAHVS45). The primary 96-well plate screens involved the dilution of spores from distinct mutant pools into fermentation substrate so that one spore in average was inoculated per well when 100 µl of medium was dispensed into each well. After inoculation, the plates were incubated for 3–4 days at 30–34° C. under static conditions in a culture box as described in WO 01/32844. A relatively concentrated micro titer plate fermentation substrate, was used to ensure high sensitivity.

The micro titer plate fermentation substrate contained:

| | |
|---|---|
| MgSO4, 7H2O | 0.3 g/l |
| K2SO4 | 0.3 g/l |
| KH2PO4 | 5.0 g/l |
| tracemetal 1 | 0.25 ml/l |
| urea | 0.65 g/l |
| yeast extract | 0.5 g/l | in demineralized water and was pH adjusted to 6.5 with NaOH.

After sterilization 5 g/l carbon-source (5000 mg/l maltose) was added.

The plates were then vacuum filtered into new microplates. The filtrated samples were spotted onto a nitrocellulose-coated microscope slide (Oncyte Art. No. 70332, Electron Microscopy Sciences, Fort Washington, Pa.) using an arrayer (GMS417, Affymetrics, Santa Clara, Calif.). The array was hybridised as described above in example 3, except that the pretreated antibody mixture was used. Also reduced antibody concentration in the hybridization step was used to further decrease background.

The array was read using an array scanner (GMS418, Affymetrics, Santa Clara, Calif.). Identification of positive hits was made with the computer programs Genesight, Imagene, and Clonetracker (Affymetrics, Santa Clara, Calif.) and positive hits was isolated on CoveN agar and retested.

For isolated transformants of interest single colonies was transferred to agar slants. Spores from agar slants were inoculated into 96-well plates with approx. $10^3$ spores per well and fermented under static conditions for 4 days at 34° C. to retest isolates. Subsequently, selected isolates were fermented in shake flasks.

In the screening of the *Humicola insolens* cDNA library 4500 clones were screened, and and of these 166 hits was recorded or identified. In the screening method positive control strains were confirmed as positive, and host strain controls were confirmed negative. Retesting including protein array with varying conditions, SDS-Page and western blot was carried out. Retest in microtiter plates by using protein arrays confirmed 83 % of the isolates as positive. In SDS-PAGE testing 42 out of 44 clones randomly selected from the 166 hits had a significant, high expression of a heterologous protein as judged by SDS-PAGE, representing >8 different molecular weights.

In western blot testing 32 out of 33 clones randomly selected from the 166 hits produced a significant band verifying these clones as hits.

Eighteen clones, representing at least eight different molecular weights was selected for sequencing and sequence data confirmed the variety of clones.

This example confirms the versatility and speed of the present invention in screening for unknown secreted compounds of a donor organism. Further, in the screening for new enzymes this method may be simultaneously combined with enzyme activity measurements so that an even further classification of the hits can be achieved.

The invention claimed is:

1. A method for screening for compounds secreted by a microorganism, comprising:
   (a) cultivating the microorganism to produce a supernatant or a supernatant including surface bound compounds of the microorganism which comprises at least 2 secreted products,
   (b) preparing a mixture of antibodies by immunizing an animal with the supernatant comprising at least 2 secreted products and isolating the mixture of antibodies formed in the animal,
   (c) providing a gene library from the microorganism,
   (d) cloning the gene library into a suitable host organism,
   (e) screening clones of the host organism using isolated antibody mixture to identify positive clones expressing a cloned gene encoding a secreted compound, and
   (f) screening positive clones for peptides or proteins having a desired function or subjecting positive clones to nucleotide sequencing in order to identify genes encoding compounds of interest.

2. The method of claim 1, wherein secreted compound is selected from the group consisting of enzymes, other proteins and peptides.

3. The method of claim 1, wherein positive clones are isolated and subjected to at least one additional screening step.

4. The method of claim 1, wherein positive clones are subjected to at least one additional screening comprising cultivating said positive clones and assaying them in a second immunoassay using the same antibodies as used in the first immunoassay to eliminate possible false positives.

5. The method of claim 1, further comprising cultivating positive clones to obtain a supernatant and using the supernatant as a starting material for additional screening steps.

6. The method of claim 1, wherein the at least two secreted products comprises an enzyme, and wherein the enzyme produced by a positive clone is isolated and tested in a functional assay for desired enzymatic activity.

7. The method of claim 1, further comprising the step of subjecting a secreted compound from a positive clone to an assay in which a desired functionality is tested for to identify clones that produce a compound exhibiting the desired functionality.

8. The method of claim 7, wherein the desired functionality is selected from wash performance, thermal stability, substrate specificity, catalytic turnover, oxidation stability, sensitivity to inhibitors, pH optimum, detergent stability, stability against microbial inactivation, toxicology, distribution profile in the human or animal body, metabolisation products, side effects, rate of metabolisation or secretion, receptor binding capacity, and antimicrobial capacity.

9. The method of claim 1, wherein step (b) includes a step of mutating a nucleotide sequence of the library.

10. The method of claim 1 wherein the supernatant comprises at least 2 secreted compounds.

11. The method of claim 1 wherein the supernatant comprises compounds bound or associated to cell membranes of the microorganism.

12. A method for screening for compounds secreted by a microorganism, comprising:
   (a) cultivating the microorganism to produce a supernatant or a supernatant including surface bound compounds of the organism which comprises at least 2 secreted products,
   (b) raising antibodies against all compounds in the supernatant or the supernatant including surface bound compounds,
   (c) providing a gene library from the organism,
   (d) cloning the gene library into a suitable host organism,
   (e) screening clones of the host organism using isolated antibody mixture to identify positive clones expressing a cloned gene encoding a secreted compound, and
   (f) screening positive clones for peptides or proteins having a desired function or subjecting positive clones to nucleotide sequencing in order to identify genes encoding compounds of interest.

* * * * *